(12) United States Patent
Chelvayohan et al.

(10) Patent No.: US 6,713,775 B2
(45) Date of Patent: Mar. 30, 2004

(54) METHOD TO CORRECT FOR SENSITIVITY VARIATION OF MEDIA SENSORS

(75) Inventors: Mahesan Chelvayohan, Lexington, KY (US); Timothy L. Anderson, Lexington, KY (US)

(73) Assignee: Lexmark International, Inc., Lexington, KY (US)

( * ) Notice: Subject to any disclaimer, the term of this patent is extended or adjusted under 35 U.S.C. 154(b) by 76 days.

(21) Appl. No.: 10/177,200

(22) Filed: Jun. 21, 2002

(65) Prior Publication Data

US 2003/0234373 A1 Dec. 25, 2003

(51) Int. Cl.[7] .................... G01N 21/00; B41J 29/393
(52) U.S. Cl. ................... 250/559.16; 250/559.18; 356/445; 347/14
(58) Field of Search .............. 250/559.16, 559.17, 250/559.18; 347/14, 19, 105, 106; 356/445, 446, 448; 399/45; 271/258.01, 259; 101/484

(56) References Cited

U.S. PATENT DOCUMENTS

| | | | |
|---|---|---|---|
| 4,019,819 A | * | 4/1977 | Lodzinski ................ 356/73 |
| 4,540,887 A | | 9/1985 | Minerd et al. |
| 4,613,235 A | | 9/1986 | Suga |
| 5,139,339 A | | 8/1992 | Courtney et al. |
| 5,764,251 A | | 6/1998 | Hashimoto |
| 6,006,668 A | | 12/1999 | Rehmann |
| 6,088,546 A | | 7/2000 | Inoue et al. |
| 6,335,501 B1 | * | 1/2002 | Khalfan .................... 209/582 |
| 6,386,669 B1 | * | 5/2002 | Schofield et al. ............ 347/14 |
| 2001/0026293 A1 | | 10/2001 | Kaneko |
| 2003/0169310 A1 | * | 9/2003 | Arguilevich et al. .......... 347/19 |

* cited by examiner

Primary Examiner—Stephone B. Allen
(74) Attorney, Agent, or Firm—Taylor & Aust, P.C.

(57) ABSTRACT

A method of correcting for sensitivity variation of media sensors includes the steps of determining a first reflectance ratio of a first calibration media having a first glossiness; determining a second reflectance ratio of a second calibration media having a second glossiness, the second glossiness being greater than the first glossiness and determining a corrected normalized reflectance ratio of an unknown media based on the first reflectance ratio of the first calibration media and the second reflectance ratio of the second calibration media.

15 Claims, 9 Drawing Sheets

METHOD TO CORRECT FOR SENSITIVITY VARIATION OF MEDIA SENSORS

BACKGROUND OF THE INVENTION

1. Field of the Invention

The present invention relates to media sensors, and, more particularly, to a method to correct for sensitivity variation of media sensors.

2. Description of the Related Art

A typical media sensor includes a single light source, such as a light emitting diode (LED), and a reflectance detector, such as a phototransistor. Also, typically, the reflectance detector is located on the same side of a media as the light source. During operation, the LED directs light at a pre-defined angle onto a material surface of the media, and the surface characteristics of the media are examined in terms of the amount of light reflected from the surface that is received by the photo detector. The presence of the media is detected based upon a predetermined amount of light reflected from the media to the reflectance detector.

Some sensors include a pair of reflectance detectors, one of the reflectance detectors being positioned to sense reflected diffuse light and a second detector positioned to sense reflected specular light. Such a sensor may be used, for example, to detect and discriminate between paper media and transparency media.

Media sensors that detect the type of media in an imaging device, such as an ink jet printer, optically measure the glossiness of the media using a media sensor similar to that described generally above. To measure the glossiness, a collimated beam of light is directed towards the media and a reflectance ratio (R) of the detected reflected specular light intensity and the detected diffusively scattered light intensity is calculated. The media sensor is initially calibrated by measuring a reflectance ratio ($R_0$) on a known gloss media. A normalized reflectance ratio (Rn) is calculated using the formula: $Rn=(R/R0)$. Normalized reflectance ratio Rn then is used to identify the media type of an unknown media by a comparison of normalized reflectance ratio Rn to a plurality of normalized reflectance ratio Rn ranges, each range being associated with a particular type of media. For example, if the media sensor is calibrated with a perfectly diffuse media, then the normalized reflectance ratio Rn ranges might be as in the following table.

TABLE 1

Media Determination Based on Reflectance Ratio $R_n$

| Rn Range | Media Type |
| --- | --- |
| Rn < 1.5 | Coated Paper |
| 1.5 < Rn < 3 | Plain Paper |
| 3 < Rn < 10 | Photo Paper |
| 10 < Rn | Transparency |

Out of the two light signals forming the ratio (R), the specularly reflected light is highly directional and its measurement is critical. The sensitivity of a media sensor to media type depends on how well the incident light is collimated and how well the specular light is captured without too much diffuse light contribution.

Variations of the optical components forming the media sensor can cause a significant spread in the sensor sensitivity. Spread in sensor sensitivity means, for example, that two sensors calibrated to the same media would result in different Rn values on a high gloss media. For example, one sensor might read the Rn value of a high glossy photo paper as Rn=8.0 while another sensor reads it as Rn=9.0. If the spread gets too large, such as if one sensor might read a photo paper as Rn=7.0 and another sensor reads the same photo paper as Rn=11.0, then the generation of a reliable test table, like that of Table 1 above, becomes difficult to achieve.

What is needed in the art is a method to correct for sensitivity variation of media sensors.

SUMMARY OF THE INVENTION

The present invention provides a method to correct for sensitivity variation of media sensors. With the present invention, a media sensor is calibrated using at least two media of different glossiness.

The invention, in one form thereof, relates to a method of correcting for sensitivity variation of media sensors. The method includes the steps of determining a first reflectance ratio of a first calibration media having a first glossiness; determining a second reflectance ratio of a second calibration media having a second glossiness, the second glossiness being greater than the first glossiness; and determining a corrected normalized reflectance ratio of an unknown media based on the first reflectance ratio of the first calibration media and the second reflectance ratio of the second calibration media In another form thereof, the present invention relates to a method of dynamically correcting for sensitivity variation of media sensors during a determination of a media type of an unknown media using a first media sensor. The method includes the steps of determining a first reflectance ratio R0 of a first calibration media having a first glossiness; providing a predetermined average normalized reflectance ratio RA of a plurality of normalized reflectance ratios R1, R2, ... RX for a second calibration media having a second glossiness, the second glossiness being greater than the first glossiness, the plurality of normalized reflectance ratios R1, R2, ... RX being generated using a plurality of media sensors; determining a second reflectance ratio R[HIGH] of the second calibration media; determining a reflectance ratio R of the unknown media; and determining a corrected normalized reflectance ratio of the unknown media based on the first reflectance ratio R0 of the first calibration media, the predetermined average normalized reflectance ratio RA of the second calibration media, the second reflectance ratio R[HIGH] of the second calibration media, and the reflectance ratio R of the unknown media.

In still another form thereof, the present invention relates to a method of determining a corrected normalized reflectance ratio of an unknown media having an unknown media type. The method includes the steps of providing a first media sensor for sensitivity correction, the first media sensor being used in determining a reflectance ratio R of the unknown media type; selecting a first calibration media having a first glossiness; selecting a second calibration media having a second glossiness, the second glossiness being greater than the first glossiness; determining a first reflectance ratio R0 of the first calibration media; determining a plurality of normalized reflectance ratios R1, R2, ... RX of the second calibration media; calculating an average normalized reflectance ratio RA of the plurality of normalized reflectance ratios R1, R2, ... RX; determining a second reflectance ratio R[HIGH] for the second calibration media; and determining a corrected normalized reflectance ratio of the unknown media based, in part, on the first reflectance ratio R0 of the first calibration media, the average normalized reflectance ratio RA of the second calibration media and the second reflectance ratio R[HIGH] for the second calibration media.

An advantage of the present invention is that the present invention permits the use of media sensors having a wider tolerance range with no decrease in media sensing accuracy.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION OF THE INVENTION

Figure 1:
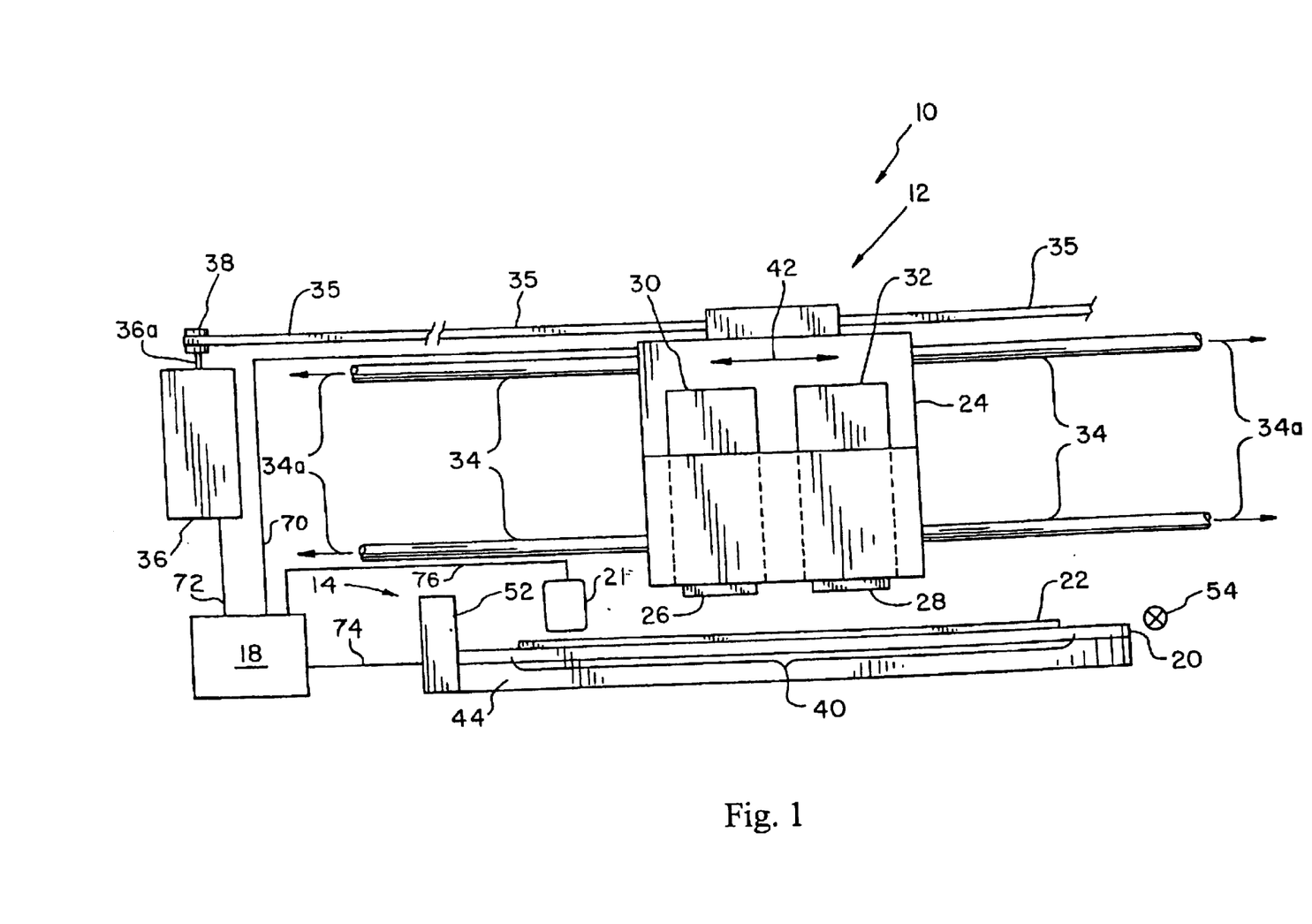
FIG. 1 is a pictorial representation of a portion of an ink jet printer including one embodiment of the present invention.

Referring now to the drawings and particularly to FIG. 1, there is shown an ink jet printer 10 embodying the present invention. Ink jet printer 10 includes a printhead carrier system 12, a feed roller unit 14, a controller 18, a mid-frame 20 and a media sensor 21.

Printhead carrier system 12 includes a printhead carrier 24 for carrying a color printhead 26 and a black printhead 28. A color ink reservoir 30 is provided in fluid communication with color printhead 26, and a black ink reservoir 32 is provided in fluid communication with black printhead 28. Printhead carrier system 12 and printheads 26, 28 may be configured for unidirectional printing or bi-directional printing.

Printhead carrier 24 is guided by a pair of guide rods 34. The axes 34a of guide rods 34 define a bi-directional scanning path for printhead carrier 24, and thus, for convenience the bi-directional scanning path will be referred to as bi-directional scanning path 34a. Printhead carrier 24 is connected to a carrier transport belt 35 that is driven by a carrier motor 36 via driven pulley 38 to transport printhead carrier 24 in a reciprocating manner along guide rods 34. Carrier motor 36 can be, for example, a direct current (DC) motor or a stepper motor. Carrier motor 36 has a rotating carrier motor shall 36a that is attached to carrier pulley 38.

The reciprocation of printhead carrier 24 transports ink jet printheads 26, 28 across a print medium sheet 22, such as paper, along bi-directional scanning path 34a to define a print zone 40 of printer 10. This reciprocation occurs in a main scan direction 42 that is parallel with bi-directional scanning path 34a, and is also commonly referred to as the horizontal direction. During each scan of printhead carrier 24, print medium sheet 22 is held stationary by feed roller unit 14.

Feed roller unit 14 includes an index roller 44 and corresponding index pinch rollers (not shown). In the embodiment shown, index roller 44 is driven by a drive unit 52. The pinch rollers apply a biasing force to hold the print medium sheet 22 in contact with respective driven index roller 44. Drive unit 52 includes a drive source, such as a stepper motor, and an associated drive mechanism, such as a gear train or belt/pulley arrangement.

Controller 18 is electrically connected to printheads 26 and 28 via a printhead interface cable 70. Controller 18 is electrically connected to carrier motor 36 via interface cable 72. Controller 18 is electrically connected to drive unit 52 via interface cable 74. Controller 18 is electrically connected to media sensor 21 via interface cable 76.

Controller 18 includes a microprocessor having an associated random access memory (RAM) and read only memory (ROM). Controller 18 executes program instructions to effect the printing of an image on print medium sheet 22, such as coated paper, plain paper, photo paper and transparency. In addition, controller 18 executes instructions to determine a media type based on information received from media sensor 21. Furthermore, controller 18 executes instructions to performing factory and/or field calibration of media sensor 21 using the method of the invention.

During operation, media sensor 21 senses the media type of print medium sheet 22 and generates reflectance signals that are supplied to controller 18 via interface cable 76. From the reflectance signals, controller 18 will determine the media type of print medium sheet 22, and based on the determined media type, will control the operation of printhead carrier 24, printheads 26 and 28, and index roller 44. For example, controller 18 controls index roller 44 via drive unit 52 to incrementally advance print medium sheet 22 in a sheet feed direction 54, toward and into a print zone 40 across mid-frame 20. At each increment of advancement of print medium sheet 22, controller 18 controls the ink ejections of printheads 26 and/or 28, and controls the reciprocation of printhead carrier 24 via motor 36. As shown in FIG. 1, sheet feed direction 54 is depicted as an X within a circle to indicate that the sheet feed direction is in a direction perpendicular to the plane of FIG. 1, toward the reader.

The media sensing capabilities of a particular media sensor serving as media sensor 21 will vary depending upon the particular light emission properties, light gathering properties, and/or light detecting properties of the particular media sensor. For example, with respect to FIGS. 2A, 2B, and 2C, more fully described below, any of media sensors 100, 120 and 130 might be incorporated into ink jet printer 10 as media sensor 21. As such, it becomes difficult to generate a single set of reflectance ratio Rn ranges, such as for example like that of Table 1 above, on which to base a media type determination that will be accurate from one printer to another printer.

Figure 2A:
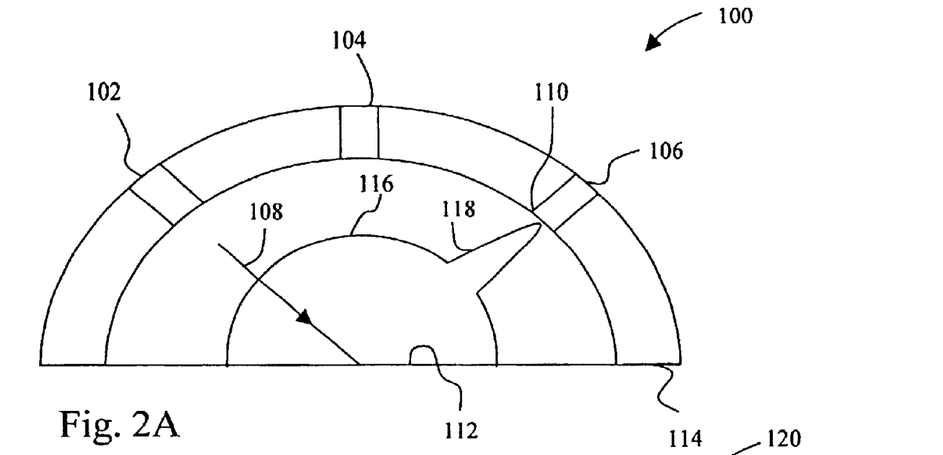
FIG. 2A diagrammatically shows an ideal high sensitive media sensor.

FIG. 2A shows an ideal high sensitive media sensor 100. Media sensor 100 includes a light source 102, such as an LED, a diffuse detector 104 and a specular detector 106. Characteristic of such a high sensitive media sensor is that light source 102 generates a collimated beam of incident light 108, and that specular detector 106 has a relatively narrow aperture 110. Incident light 108 impinges media surface 112 of media 114 and is separated into reflected diffuse light components 116 and reflected specular light components 118. Specular light components 118 are received through the narrow aperture 110 of specular detector 106. In this ideal design, a minimum amount of reflected diffuse light components 116 is received by specular detector 106.

Figure 2B:
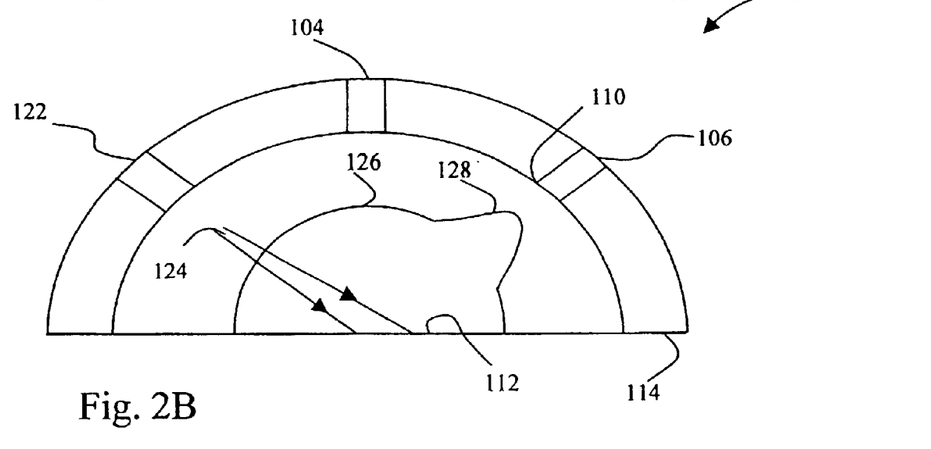
FIG. 2B diagrammatically shows a media sensor having inferior light generating properties as compared to the media sensor of FIG. 2A.

If, as shown in FIG. 2B, a media sensor 120 replaces light source 102 with a light source 122 having inferior light generating properties, the incident light 124 is not collimated. Incident light 124 impinges media surface 112 of media 114 and is separated into reflected diffuse light components 126 and reflected specular light components 128. With media sensor 120, as incident light 124 impinges surface 112 of media 114, the reflected specular light components 128 become broader and the amount of specular light components 128 that enter aperture 110 is reduced. As a result, media sensor 120 is less sensitive to media type than was media sensor 100.

Figure 2C:
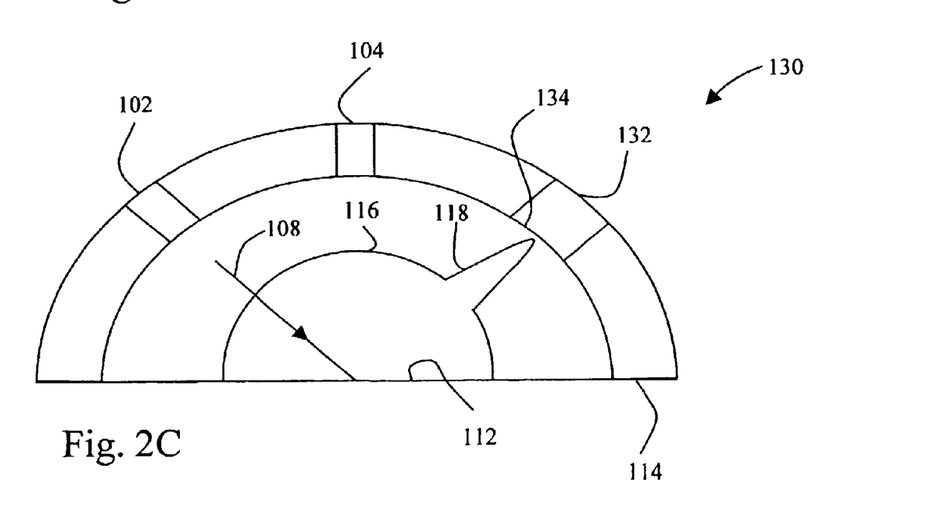
FIG. 2C diagrammatically shows a media sensor having an detector aperture that is wider than the detector aperture of FIG. 2A.

Similarly, if, as shown in FIG. 2C, a media sensor 130 replaces specular detector 106 with a specular detector 132 having an aperture 134 that is wider than aperture 110 of FIG. 2A, and in turn wider than the reflected specular light components 118, more of the reflected diffuse light components 116 are allowed to enter into specular detector 132 through aperture 134, which as a result, also makes media sensor 130 less sensitive to media type than was media sensor 100.

Figure 3:
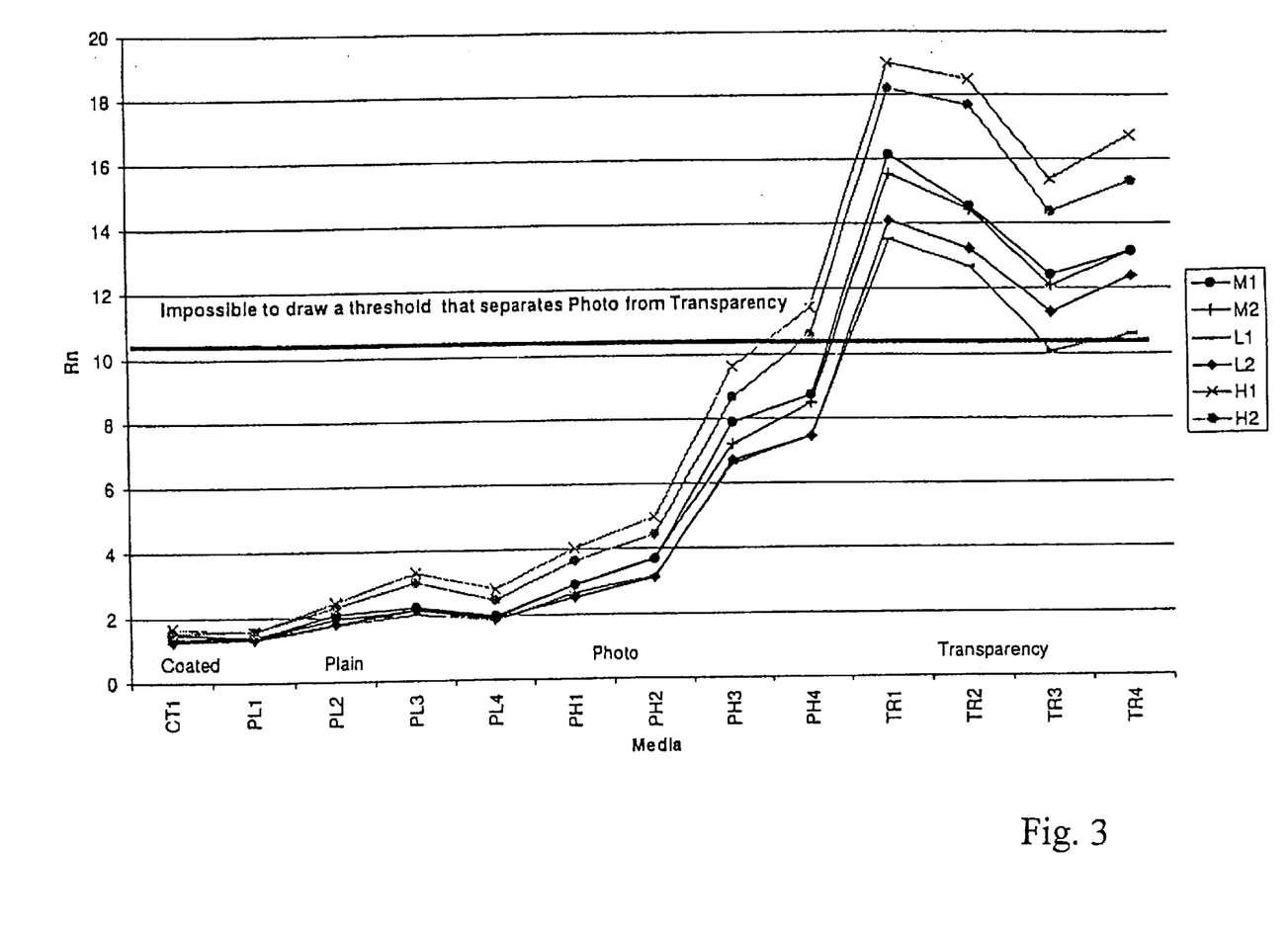
FIG. 3 shows a graph of exemplary glossiness data measured on different media tyees in terms of normalized reflectance ratio Rn, prior to implementing the present invention.

FIG. 3 shows a graph of exemplary glossiness data measured on different media types in terms of reflectance ratio Rn using low sensitivity sensors (L1, L2), medium sensitivity sensors (M1, M2) and high sensitivity sensors (H1, H2). The various media types identified are coated paper CT1; various plain papers PL1, PL2, PL3, PL4; various photo papers PH1, PH2, PH3, PH4, and various transparencies TR1, TR2, TR3, TR4. As depicted on the graph, the normalized reflectance ratio Rn calculated based on the measured R for photo paper PH4 using either high sensitivity sensor H1 or high sensitivity sensor H2 is higher than the value measured for transparency TR3 using low sensitivity sensor L1. In other words, it is impossible to draw a horizontal line from the vertical normalized reflectance ratio Rn axis that separates the photo media from the transparency media in this situation.

Figure 4:
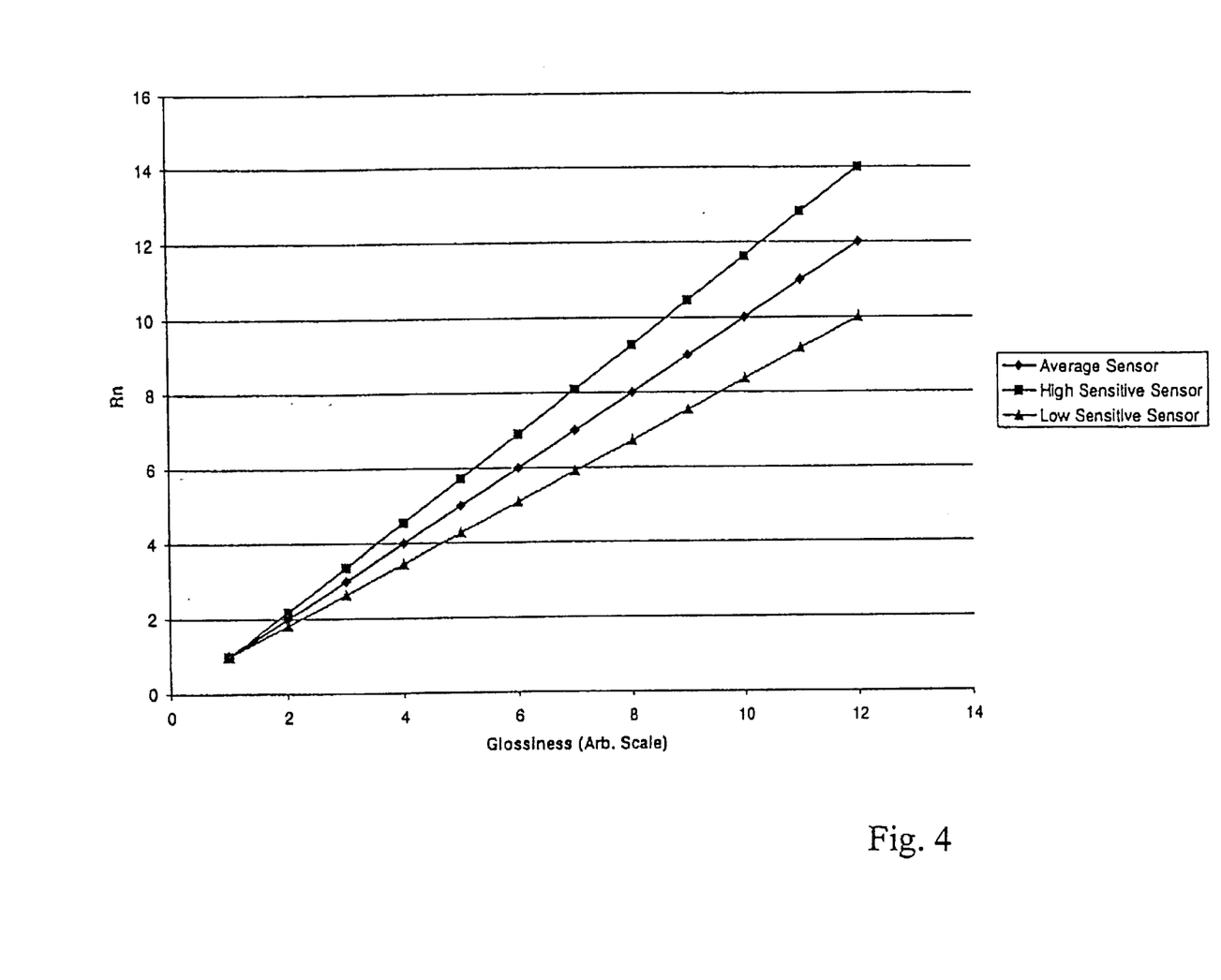
FIG. 4 shows a graph of normalized reflectance ratio Rn versus glossiness for each of a low sensitivity sensor L1; an average, i.e., medium sensitivity sensor M1; and a high sensitivity sensor H1, before implementing the present invention.
Figure 5:
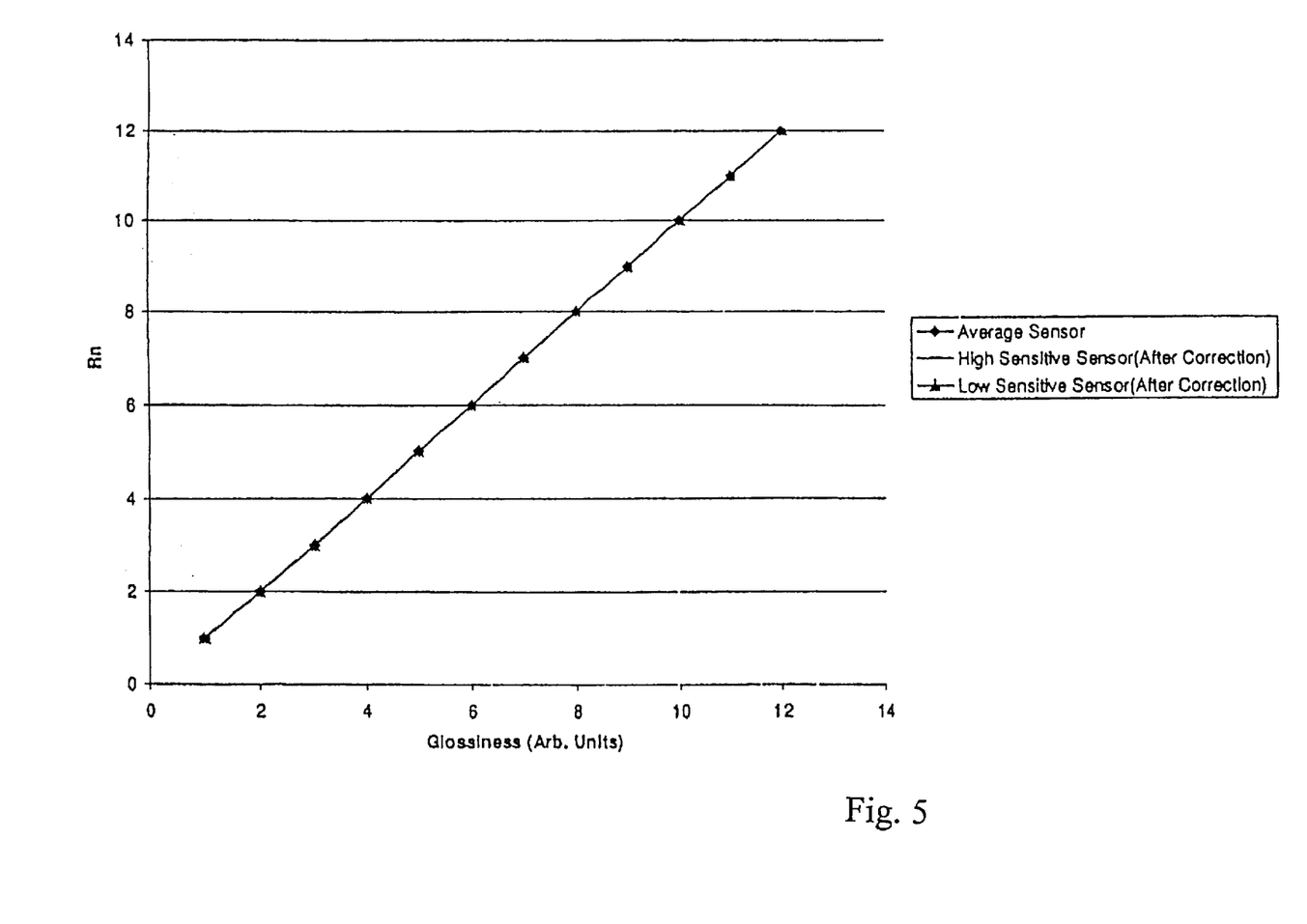
FIG. 5 shows a graph of normalized reflectance ratio Rn versus glossiness for each of the low sensitivity sensor L1; the average, i.e., medium sensitivity sensor M1; and high sensitivity sensor H1, after implementing the present invention.

FIG. 4 shows a graph of normalized ratio reflectance ratio Rn versus glossiness for each of low sensitivity sensor L1; an average, i.e., medium, sensitivity sensor M1; and high sensitivity sensor H1, before using the media sensor sensitivity correction method of the present invention. As shown, the slope of the curve for low sensitivity sensor L1 is less than the slope of the curve for medium sensitivity sensor M1. Also, the slope of the curve for high sensitivity sensor H1 is greater than the slope of the curve for medium sensitivity sensor M1. However, as shown in FIG. 5, by incorporating the media sensor sensitivity correction method of the present invention, the slopes of the respective curves for low sensitivity sensor L1; average, i.e., medium, sensitivity sensor M1; and high sensitivity sensor H1 become substantially equal, and ideally, the respective slopes are identical.

In general, in order to provide for media sensor sensitivity correction. the present invention generates corrected normalized reflectance ratio Rn values that compensate for variations in the sensitivity of the media sensors, such as that of media sensors L1, L2, M1, M2, H1 and H2, described above. As such, for example, it will be possible to use any of media sensors L1, L2, M1, M2, H1, H2, which may possess reflectance characteristics like that of one media sensors 100, 120, 130 of FIGS. 2A–2C, as media sensor 21 in the various printers manufactured using a common design, e.g., printers of a common printer model, or family of printers, without the misidentification of certain types of media, as would occur in the absence of the present invention, with respect to low sensitivity sensor L1 and either of high sensitivity sensors H1, H2, as described above with reference to FIG. 3. Thus, advantageously, the present invention permits the use of media sensors having a wider tolerance range with no decrease in media sensing accuracy, thereby permitting an opportunity to reduce printer manufacturing costs.

As one aspect of the present invention, an algorithm is used for calculating a corrected normalized reflectance ratio Rn by calibrating the media sensor in use using media of two different media glossiness, such as for example, coated paper (low gloss) and transparency media (high gloss).

Figure 6:
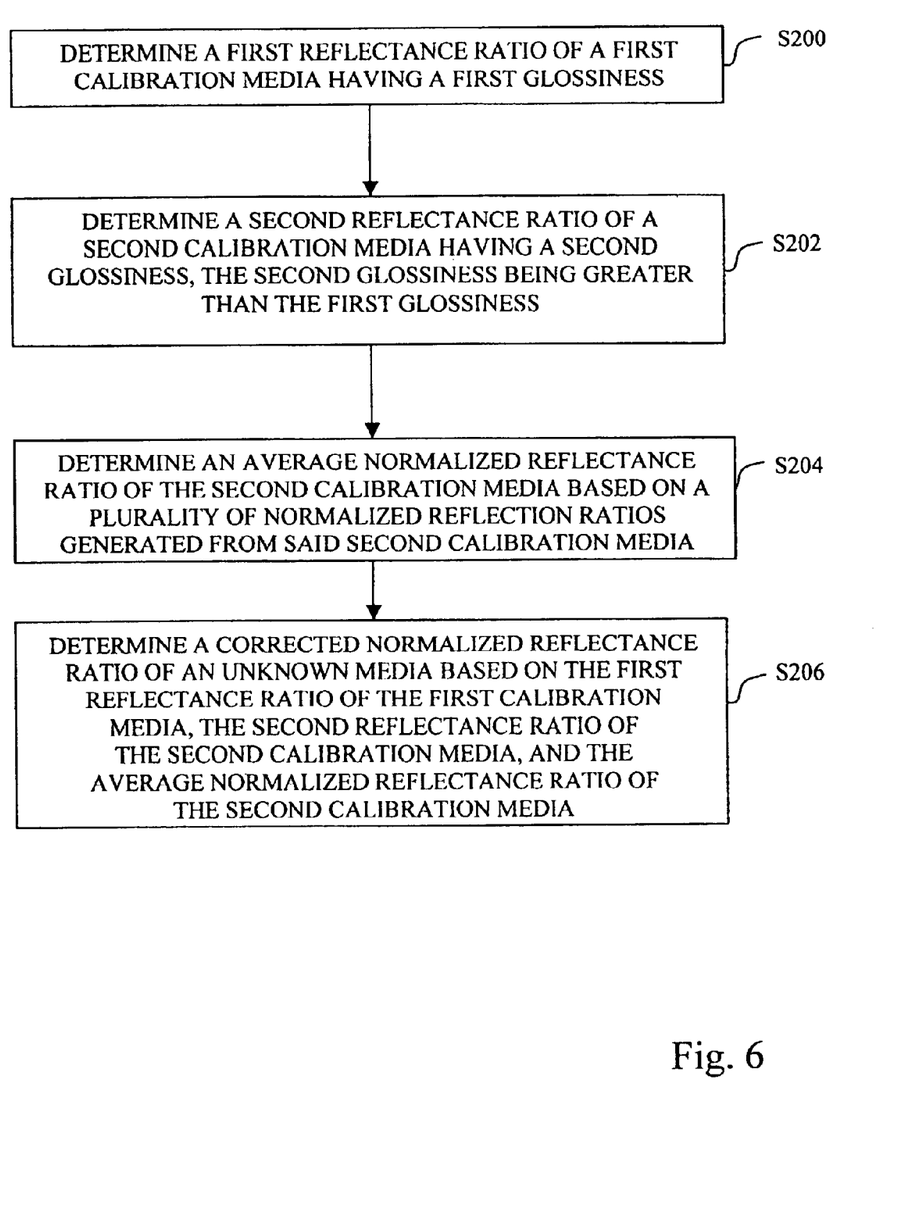
FIG. 6 is flowchart of one embodiment of the present invention.

A method of one embodiment of the invention is described below in relation to the flowchart of FIG. 6. The flowchart of FIG. 6 is directed to a method of correcting for sensitivity variation of media sensors.

At step S200, the process determines a first reflectance ratio R0 of a first calibration media having a glossiness G1. Such a first calibration media could be, for example, coated media CT1. The determination of the first reflectance ratio can be achieved, for example, by measuring the glossiness G1 of the first calibration media with media sensor 21, and by calculating the first reflectance ratio R0 based on the measured result using controller 18. For example, to determine the first reflectance ratio R0, media sensor 21 detects the amount of reflected specular light and detects the amount of reflected diffuse light that is reflected from the first calibration media, and provides signals corresponding thereto to controller 18, which in turn calculates the first reflectance ratio R0.

At step S202, the process determines a second reflectance ratio R[HIGH] of a second calibration media having a glossiness G2. The second calibration media will be selected so that glossiness G2 is greater than glossiness G1 of the first calibration media. Such a second calibration media could be, for example, transparency TR2. Second reflectance ratio R[HIGH] is determined by measuring the glossiness G2 of the second calibration media with media sensor 21, and by calculating the second reflectance ratio R[HIGH] based on the measured result using controller 18. For example, to determine the second reflectance ratio R[HIGH], media sensor 21 detects the amount of reflected specular light and detects the amount of reflected diffusse light that is reflected from the second calibration media, and provides signals corresponding thereto to controller 18, which in turn calculates the second reflectance ratio R[HIGH].

At step S204, an average normalized reflectance ratio RA of the second calibration media is determined based on a plurality of normalized reflectance ratios (R[HIGH]/R0) generated using a corresponding plurality of media sensors, such as media sensors L1, L2, M1, M2, H1, H2 having characteristics, for example, like or varying from that of media sensors 100, 120 and 130 of FIGS. 2A–2C. For purposes of step S204, each reflectance ratio R0 and R[HIGH] is determined by each of the plurality of media sensors, such as media sensors L1, L2, M1, M2, H1, H2, using the approach described above with respect to step S200 and step S202. Controller 18 then normalizes each of the plurality of reflectance ratios R[HIGH] using their respective reflectance ratio R0, and calculates therefrom the average normalized reflectance ratio RA of the second calibration media.

At step S206, in general, the process determines a corrected normalized reflectance ratio Rn(CORRECTED), of an unknown media based on first reflectance ratio R0 of the first calibration media, the second reflectance ratio R[HIGH] of the second calibration media and the average normalized reflectance ratio RA of the second calibration media. As an example of such a determination at step 206, controller 18 executes program steps to perform the relationship:

$$Rn(\text{CORRECTED})=1+((R/R0)-1)\times(RA-1)/((R[\text{HIGH}]/R0)-1),$$

wherein:

Rn[CORRECTED] is the corrected normalized reflectance ratio of the unknown media;

R is a measured reflectance ratio of the unknown media by a first media sensor, such as media sensor 21;

R0 is the first reflectance ratio of the first calibration media determined using media sensor 21;

R[HIGH] is the second reflectance ratio of the second calibration media determined using media sensor 21; and RA is the average of the plurality of normalized reflectance ratios of the second calibration media determined using a corresponding plurality of media sensors.

Figure 7:
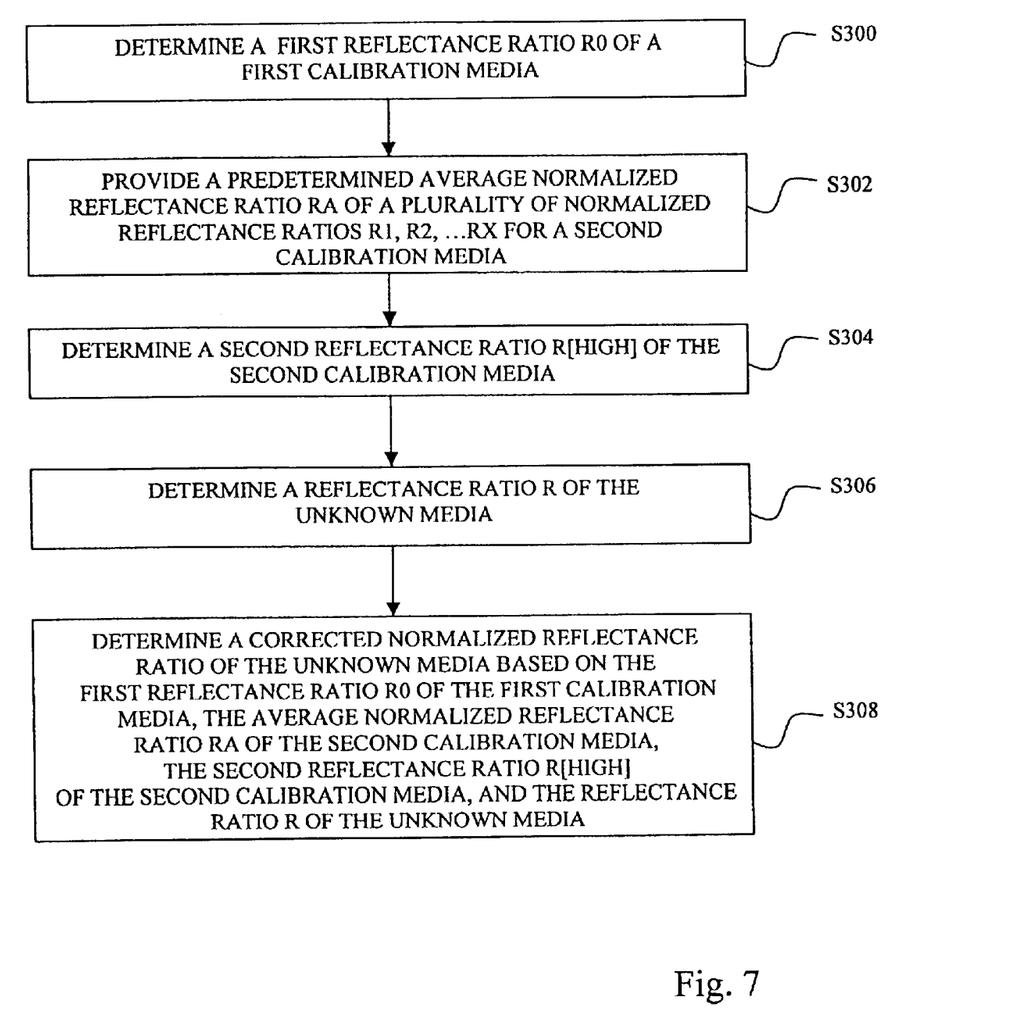
FIG. 7 is flowchart of another embodiment of the present invention.

A method of another embodiment of the invention is described below in relation to the flowchart of FIG. 7. The flowchart of FIG. 7 is directed to a method of dynamically correcting for sensitivity variation of media sensors during a determination of a media type of an unknown media using a first media sensor, such as media sensor 21 of FIG. 1.

At step S300, the process begins with determining a first reflectance ratio R0 of a first calibration media having a first glossiness G1. Such a first calibration media could be, for example, coated media CT1. The determination of the first reflectance ratio can be achieved, for example, by measuring the glossiness G1 of the first calibration media with media sensor 21, and by calculating the first reflectance ratio R0 based on the measured result using controller 18. The reflectance ratio R0 may be stored, for example, in the memory associated with controller 18.

At step S302, the process provides a predetermined average normalized reflectance ratio RA of a plurality of normalized reflectance ratios R1, R2, . . . RX for a second calibration media having a second glossiness G2. The second calibration media is selected such that the second glossiness G2 is greater than the first glossiness G1. The plurality of normalized reflectance ratios R1, R2, . . . RX may be generated, for example, using a corresponding plurality of media sensors, such as media sensors L1, L2, M1, M2, H1, H2 having characteristics, for example, like or varying from that of media sensors 100, 120 and 130 of FIGS. 2A–2C. This predetermined average normalized reflectance ratio RA may be stored, for example, in the memory associated with controller 18.

At step S304, the process determines a second reflectance ratio R[HIGH] of the second calibration media having a glossiness G2. Such a second calibration media could be, for example, transparency TR2. Second reflectance ratio R[HIGH] is determined by measuring the glossiness G2 of the second calibration media with media sensor 21, and by calculating the second reflectance ratio R[HIGH] based on the measured result using controller 18. The second reflectance ratio R[HIGH] may be stored, for example, in the memory associated with controller 18.

At step S306, using first media sensor 21 and controller 18, a reflectance ratio R of the unknown media is determined. For example, to determine the reflectance ratio R, media sensor 21 detects the amount of reflected specular light and detects the amount of reflected diffuse light that is reflected from the unknown media, and provides signals corresponding thereto to controller 18, which in turn calculates the reflectance ratio R.

At step S308, controller 18 determines a corrected normalized reflectance ratio of the unknown media based on the first reflectance ratio R0 of the first calibration media, the average normalized reflectance ratio RA of the second calibration media, the second reflectance ratio R[HIGH] of the second calibration media, and the reflectance ratio R of the unknown media. As an example of such a determination at step 308, controller 18 executes program steps to perform the arithmetic relationship:

$$Rn(\text{CORRECTED})=1+((R/R0)-1)\times(RA-1)/((R[\text{HIGH}]/R0)-1),$$

wherein:

Rn[CORRECTED] is the corrected normalized reflectance ratio of the unknown media;

R is a measured reflectance ratio of the unknown media by a first media sensor, such as media sensor 21;

R0 is the first reflectance ratio of the first calibration media determined using media sensor 21;

R[HIGH] is the second reflectance ratio of the second calibration media determined using media sensor 21; and RA is the average of the plurality of normalized reflectance ratios of the second calibration media determined using a corresponding plurality of media sensors.

Figure 9:
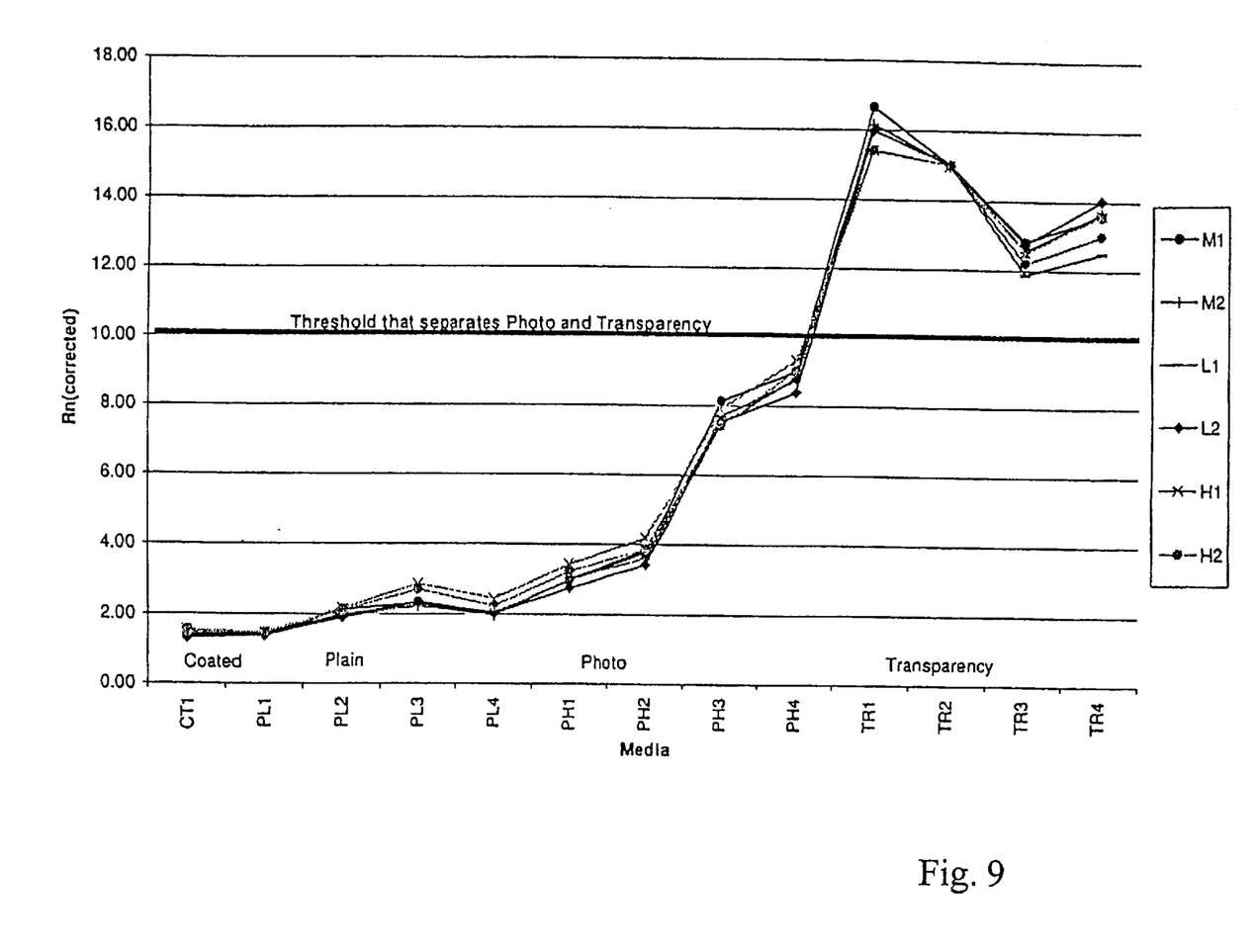
FIG. 9 shows a graph of exemplary glossiness data measured on different media types in terms of reflectance ratio Rn after implementing the present invention.

Thereafter, controller 18 can determine the media type of the unknown media by comparing the corrected normalized reflectance ratio Rn[CORRECTED] to a set of predetermined normalized reflectance ratio Rn ranges, such as those in Table 1, above. As shown in Table 1, each of the predetermined normalized reflectance ratio ranges represent one of a plurality of media types, e.g., coated paper CT1; various plain papers PL1, PL2, PL3, PL4; various photo papers PH1, PH2, PH3, PH4, and various transparencies TR1, TR2, TR3, TR4, as represented in the graph of FIG. 9.

Figure 8:
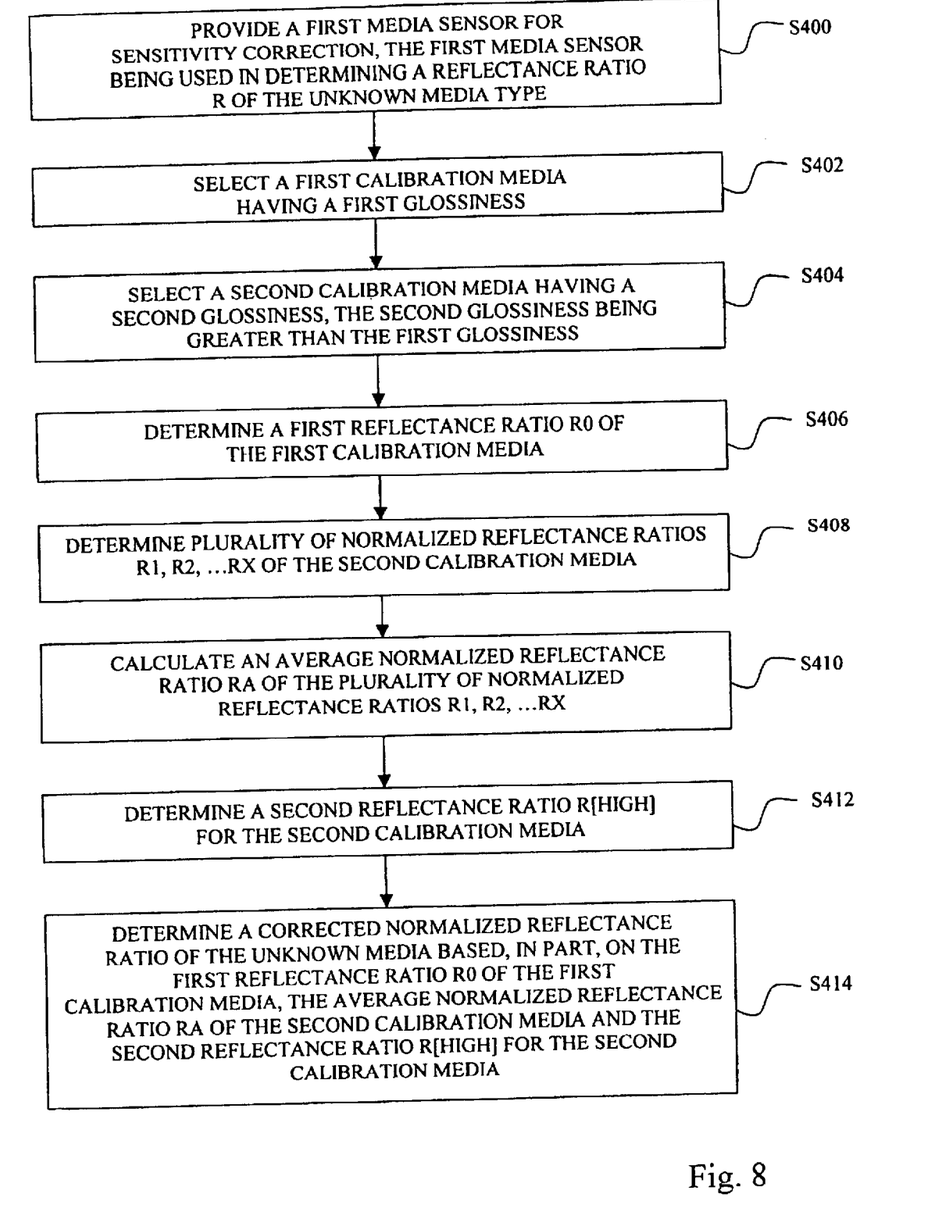
FIG. 8 is flowchart of still another embodiment of the present invention.

A method of another embodiment of the invention is described below in relation to the flowchart of FIG. 8. The flowchart of FIG. 8 is directed to a method of determining a corrected normalized reflectance ratio of an unknown media having an unknown media type.

At step S400, the process begins with providing a first media sensor for sensitivity correction, such as media sensor 21. The media sensor 21 is used in determining a reflectance ratio R of the unknown media type.

At step S402, the process selects a first calibration media, such as coated paper CT1, having a first glossiness G1.

At step S404, the process selects a second calibration media, such as transparency TR2, having a second glossiness. The second glossiness G2 is greater than the first glossiness G1.

At step S406, the process determines a first reflectance ratio R0 of the first calibration media. The determination of the first reflectance ratio R0 is achieved by measuring the glossiness G1 of the first calibration media with media sensor 21, and by calculating the first reflectance ratio R0 based on the measured result using controller 18.

At step S408, the process determines a plurality of normalized reflectance ratios R1, R2, . . . RX of the second calibration media using a plurality of media detectors.

At step S410, the process calculates an average normalized reflectance ratio RA of the plurality of normalized reflectance ratios R1, R2, . . . RX.

At step S412, the process determines a second reflectance ratio Rn[HIGH] for the second calibration media. Second reflectance ratio R[HIGH] is determined by measuring the glossiness G2 of the second calibration media with media sensor 21, and by calculating the second reflectance ratio R[HIGH] based on the measured result using controller 18.

At step S414, the process determines a corrected normalized reflectance ratio of the unknown media based, in part, on the first reflectance ratio R0 of the first calibration media, the average normalized reflectance ratio RA of the second calibration media and the second reflectance ratio R[HIGH] for the second calibration media. At step S414, for example, the corrected normalized reflectance ratio of the unknown media can be determined by a relationship expressed as:

$$Rn(CORRECTED)=1+((R/R0)-1)\times(RA-1)/((R[HIGH]/R0)-1),$$

wherein:
  Rn[CORRECTED] is the corrected normalized reflectance ratio of the unknown media;
  R is a measured reflectance ratio of the unknown media by a first media sensor, such as media sensor 21;
  R0 is the first reflectance ratio of the first calibration media determined using media sensor 21;
  R[HIGH] is the second reflectance ratio of the second calibration media determined using media sensor 21; and
  RA is the average of the plurality of normalized reflectance ratios of the second calibration media determined using a corresponding plurality of media sensors.

As a result of implementing the present invention, as described above with respect to the embodiments of FIGS. 6, 7 and 8, the beneficial effects thereof can be appreciated by viewing the graph of FIG. 9. As show, and unlike the graph of FIG. 3, it is apparent that the individual gloss curves associated with the media types of coated paper CT1; various plain papers PL1, PL2, PL3, PL4; various photo papers PH1, PH2, PH3, PH4, and various transparencies TR1, TR2, TR3, TR4, are now tighter, and there is a definite separation between the various media types. As such, each of the various types of media can be accurately detected using any of the media sensors L1, L2, M1, M2, H1, H2 as media sensor 21 of FIG. 1.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of correcting for sensitivity variation of media sensors, comprising the steps of:
   (a) determining a first reflectance ratio of a first calibration media having a first glossiness;
   (b) determining a second reflectance ratio of a second calibration media having a second glossiness, said second glossiness being greater than said first glossiness;
   (c) determining a corrected normalized reflectance ratio of an unknown media based on said first reflectance ratio of said first calibration media and said second reflectance ratio of said second calibration media.

2. The method of claim 1, wherein step (a) comprises the step of measuring said first glossiness of said first calibration media with a first media sensor and calculating said first reflectance ratio.

3. The method of claim 2, wherein step (b) comprises the step of measuring said second glossiness of said second calibration media with said first media sensor and calculating said second reflectance ratio.

4. The method of claim 1, further comprising the step of determining an average normalized reflectance ratio of said second calibration media based on a plurality of normalized reflectance ratios generated from said second calibration media, said average normalized reflectance ratio of said second calibration media being used in determining said corrected normalized reflectance ratio of said unknown media.

5. The method of claim 4, wherein said plurality of normalized reflectance ratios are generated using a corresponding plurality of media sensors.

6. The method of claim 1, wherein step (c) is performed using the equation:

$$Rn(CORRECTED)=1+((R/R0)-1)\times(RA-1)/((R[HIGH]/R0)-1),$$

wherein:
  Rn[CORRECTED] is a corrected normalized reflectance ratio of said unknown media;
  R is a measured reflectance ratio of the unknown media by said first media sensor;
  R0 is said first reflectance ratio of said first calibration media determined using said first media sensor;
  R[HIGH] is said second reflectance ratio of said second calibration media determined using said first media sensor, and
  RA is said average normalized reflectance ratio of said second calibration media determined using a plurality of media sensors.

7. A method of dynamically correcting for sensitivity variation of media sensors during a determination of a media type of an unknown media using a first media sensor, comprising the steps of:
   determining a first reflectance ratio R0 of a first calibration media having a first glossiness;
   providing a predetermined average normalized reflectance ratio RA of a plurality of normalized reflectance ratios R1, R2, . . . RX for a second calibration media having a second glossiness, said second glossiness being greater than said first glossiness, said plurality of normalized reflectance ratios R1, R2, . . . RX being generated using a plurality of media sensors;

determining a second reflectance ratio R[HIGH] of said second calibration media;

determining a reflectance ratio R of said unknown media; and determining a corrected normalized reflectance ratio of said unknown media based on said first reflectance ratio R0 of said first calibration media, said predetermined average normalized reflectance ratio RA of said second calibration media, said second reflectance ratio R[HIGH] of said second calibration media, and said reflectance ratio R of said unknown media.

8. The method of claim 7, wherein said determining step is performed using the equation Rn(CORRECTED)=1+((R/R0)−1)×(RA−1)/((R[HIGH]/R0)−1), wherein RN[CORRECTED] is said corrected normalized reflectance ratio of said unknown media.

9. The method of claim 7, wherein said reflectance ratio R of said unknown media is determined using said first media sensor.

10. The method of claim 9, wherein said first reflectance ratio R0 is determined using said first media sensor.

11. The method of claim 10, wherein said second reflectance ratio R[HIGH] is determined using said first media sensor.

12. The method of claim 7, wherein said media type is determined by comparing said corrected normalized reflectance ratio to a set of predetermined reflectance ratio ranges, each of said predetermined reflectance ratio ranges representing one of a plurality of media types.

13. The method of claim 12, wherein said plurality of media types include at least one of coated media, plain paper, photo paper and a transparency.

14. A method of determining a corrected normalized reflectance ratio of an unknown media having an unknown media type, comprising the steps of:

providing a first media sensor for sensitivity correction, said first media sensor being used in determining a reflectance ratio R of said unknown media type;

selecting a first calibration media having a first glossiness;

selecting a second calibration media having a second glossiness, said second glossiness being greater than said first glossiness;

determining a first reflectance ratio R0 of said first calibration media;

determining a plurality of normalized reflectance ratios R1, R2, . . . RX of said second calibration media;

calculating an average normalized reflectance ratio RA of said plurality of normalized reflectance ratios R1, R2, . . . RX;

determining a second reflectance ratio R[HIGH] for said second calibration media; and determining a corrected normalized reflectance ratio of said unknown media based, in part, on said first reflectance ratio R0 of said first calibration media, said average normalized reflectance ratio RA of said second calibration media and said second reflectance ratio R[HIGH] for said second calibration media.

15. The method of claim 14, wherein said corrected normalized reflectance ratio of said unknown media is determined by a relationship expressed as; Rn(CORRECTED)=1+((R/R0)−1)×(RA−1)/(R[HIGH]/R0)−1), and wherein Rn[CORRECTED] is said corrected normalized reflectance ratio of said unknown media.

* * * * *